US011717499B2

(12) United States Patent
Reznik et al.

(10) Patent No.: US 11,717,499 B2
(45) Date of Patent: Aug. 8, 2023

(54) ADMINISTRATION OF N,N-DIMETHYLACETAMIDE FOR THE TREATMENT OF PRETERM BIRTH

(76) Inventors: Sandra Eve Reznik, Larchmont, NY (US); Charles R. Ashby, Jr., Miller Place, NY (US); Jerome Owen Cantor, Brooklyn, NY (US)

( * ) Notice: Subject to any disclaimer, the term of this patent is extended or adjusted under 35 U.S.C. 154(b) by 881 days.

(21) Appl. No.: 13/536,946

(22) Filed: Jun. 28, 2012

(65) Prior Publication Data

US 2014/0005272 A1     Jan. 2, 2014

Related U.S. Application Data

(60) Provisional application No. 61/571,433, filed on Jun. 28, 2011.

(51) Int. Cl.
*A61K 31/16*     (2006.01)
(52) U.S. Cl.
CPC ................................. *A61K 31/16* (2013.01)
(58) Field of Classification Search
None
See application file for complete search history.

(56) References Cited

U.S. PATENT DOCUMENTS

| | | | | |
|---|---|---|---|---|
| 3,068,145 | A * | 12/1962 | Glenn | 514/171 |
| 3,070,502 | A * | 12/1962 | Sponnoble | A61K 31/65 |
| | | | | 514/152 |
| 3,627,886 | A * | 12/1971 | Newmark | 514/27 |
| 2008/0213211 | A1 * | 9/2008 | Carter | A61K 31/7076 |
| | | | | 424/85.1 |

FOREIGN PATENT DOCUMENTS

WO     WO-9407496 A1 *     4/1994           C07D 221/20

OTHER PUBLICATIONS

Klebanoff et al. "The Role of Inflammation in Preterm Birth-Focus on Periodontitis", BJOG, 2006; 113(Suppl.3):43-45.*
Sundaram et al. Abstract F-247. "N,N-Dimethylacetamide Controls Infection-Associated Preterm Birth in a Murine Model". Reproductive Sciences. Mar. 2011; 18(4, Supplement):244A. (Year: 2011).*
Sundaram et al. Abstract O-163. "N,N-Dimethylacetamide (DMA) Prevents Preterm Birth in a Murine Model by Up-Regulating Interleukin 10 (IL-10)". Reproductive Sciences. Mar. 2012; 19(3, Supplement):120A. (Year: 2012).*
Reproductive Sciences [Online]. vol. 18, Supplement Issue 3, Mar. 2011. [Retrieved Apr. 7, 2022]. Retrieved from the Internet: <URL: https://www.link.springer.com/journal/43032/volumes-and-issues/18-3/supplement>. pp. 1-2. (Year: 2022).*
Huter et al. "Die Beeinflussung der Spontanwehentatigkeit der schwangeren Ratte durch Valium (Diazepam) und seine Losungsvermittler (in-vivo Messungen mittels interner Tokometrie)". Geburtshilfe und Frauenheilkunde, 1967; 27(6):609-615. (Year: 1967).*
USPTO English Translation of Huter et al. (Geburtshilfe und Frauenheilkunde, 1967; 27(6):609-615). pp. 1-18. (Year: 2022).*
CAS Entry for Huter et al. (Geburtshilfe und Frauenheilkunde, 1967; 27(6):609-615). ISSN: 0016-5751. One page. (Year: 2022).*
Reagan-Shaw et al. "Dose Translation from Animal to Human Studies Revisited". FASEB J. 2007; 22:659-661. (Year: 2007).*
Aungst et al., "The Influence of Donor and Reservoir Additives on Caco-2 Permeability and Secretory Transport of HIV Protease Inhibitors and other Lipophilic Compounds", 2000, Pharmaceutical Research, 1175-1180, vol. 17, No. 10.
Beyhl et al., "Action of N,N-Diethylacetamide on Hepatic Microsomal Drug-Metabolizing Enzymes", Fd Cosmet. Toxicol., 1981, pp. 627 to 629, vol. 19, Pergamon Press Ltd., Great Britain.
Eichhorst, et al., "Health-Related Quality of Life in Younger Patients With Chronic Lymphocytic Leukemia Treated With Fludarabine Plus Cyclophosphamide or Fludarabine Alone for First-Line Therapy: A Study by the German CLL Study Group", Journal of Clinical Oncology, May 1, 2007, pp. 1722-1731, vol. 25, No. 13, American Society of Clinical Oncology, Munich, Germany.
Hundley et al., "Dimethylacetamide pharmacokinetics following inhalation exposures to rats and mice", Toxicology Letters, 1994, pp. 213-225, vol. 73, Elsevier.
Odink et al., "Platelet Preservation. I. The Use of Decrease in Light Absorbance as a Screening Method in Cryopreservation Studieson Human Platelets", Cryobiology, 1977, pp. 519 to 528, vol. 14, Academic Press, Inc.
Puneet et al., "SphK1 Regulates Proinflammatory Responses Associated with Endotoxin and Polymicrobial Sepsis", Science, 2010, pp. 1290 to 1294, vol. 328.
Ulloa et al., "Ethyl pyruvate prevents lethality in mice with established lethal sepsis and systemic inflammation", Proceedings of the National Academy of Sciences, Sep. 17, 2002, pp. 12351 to 12356, vol. 99, No. 19.
Wadgaonkar et al., "Differential regulation of sphingosine kinases 1 and 2 in lung injury", Am J Physiol Lung Cell Mol Physiol, 2009, pp. L603 to L613, vol. 296.
Weighardt et al., "Role of Toll-like receptor responses for sepsis pathogenesis", Immunobiology, 2008, pp. 715 to 722, vol. 212, Elsevier.
Bisacchi, et al. "A New-Class Antibacterial!Almost. Lessons in Drug Discovery and Development: A Critical Analysis of More than 50 Years of E!ort toward ATPase Inhibitors of DNA Gyrase and Topoisomerase IV", ACS Infectious Diseases, 2015, 1, 4-41.
J.M. Conchie et al., "The incidence of staining of permanent teeth by the tetracyclines," C.M.A. Journal, 1970 vol. 102; pp. 351-355. Label for tetracycline hydrochloride obtained from the National Institutes of Health, United States National Library of Medicine Drug Labeling Archives.

(Continued)

*Primary Examiner* — Leslie A. Royds Draper
(74) *Attorney, Agent, or Firm* — Storella, P.C.

(57) ABSTRACT

The subject invention is directed to the treatment of inflammatory disorders by administration of N,N-dimethylacetamide and its mono-methylated metabolites. The compounds are useful in the management or treatment of inflammatory disorders, such as generative inflammation associated preterm labor and premature rupture of membranes leading to preterm birth.

18 Claims, 9 Drawing Sheets

(56) References Cited

OTHER PUBLICATIONS

Godfrey, John C., et al., "Structure-Activity Relationships in Coumermycins", Bristol Laboratories, Division of Bristol-Myers Company, Syracuse, New York, pp. 231-296.

Holt, Roxane, et al., "The Molecular Mechanisms of Cervical Ripening Differ between Term and Preterm Birth", Endocrinology, Mar. 2011, 152(3): 1036-1046, endo.endojournals.org, Downloaded from https://academic.oup.com/endo/article/152/3/1036/2457410 by Albert Einstein Coll Med—Cardozo—Yeshiva Univ Libraries user on Apr. 19, 2021.

Kimura, Masayasu, et al., "Mouse Granuloma Pouch Induced by Freund's Complete Adjuvant With Croton Oil", J. Pharmacobio-Dyn., 8, 393-400, 1985, Dept of Chem Pharm, Faculty of Pharm Sciences, Toyama Medical and Pharmaceutical Univ, Japan.

Macones, George A., MD., et al., "The controversy surrounding indomethacin for tocolysis:", Am J Obstet Gynecol, vol. 184, No. 3, Feb. 2001, pp. 264-272.

Norwitz, Errol R., MD, PhD., et al., "Antibiotics in Pregnancy: Are They Safe?", editorial, Reviews in Obstetrics & Gynecology, vol. 2, No. 3, 2009, pp. 135-136.

Peltier, Morigan R., "Immunology of term and preterm labor", review in Reproductive Biology and Endocrinology, 2003, 1:122, BioMed Central, 11 pages.

Simhan, Hyagriv N., MD., et al., "Elevated vaginal pH and neutrophils are associatedstrongly with early spontaneous preterm birth", Am J Obstet Gynecol, Oct. 2003, vol. 189, No. 4, pp. 1150-1154.

Streit, Markus, et al., "Contact dermatitis: clinics and pathology", Acta Odontol Scand 2001;59: 309-314 .Oslo. ISSN 0001-6357, Dermatological University Clinic, Switzerland.

Wood, Stephen et al., "Periodontal disease and spontaneous preterm birth: a case control study", BMC Pregnancy and Childbirth research article, BioMed Central, doi:10.1186/1471-2393-6-24, Jul. 19, 2006, 8 pages.

Houben, Michiel L. et al., The association between intrauterine inflammation and spontaneous vaginal delivery at term: A cross-sectional study, PLoS One, Aug. 2009, vol. 4, Issue, 8.

Weiner, Carl P. et al., Basic Science: Obstetrics—Human effector/initiator gene sets that regulate myometrial contractility during term and preterm labor, May 2010, American Journal of Obstetrics & Gynecology.

Tattersall, Mark et al., Pro-labour myometrial gene expression: are preterm labour and term labour the same? Reproduction Research, 2008 Society for Reproduction and Fertility, Reproduction (2008) 135 569-579.

Pryde, Peter G. et al., Adverse and Beneficial Effects of Tocolytic Therapy, Seminars in Perinatology, vol. 25, No. 5 (October), 2001: pp. 316-340.

Sciscione, Anthony C. et al., Tocolysis of preterm contractions does not improve preterm delivery rate or perinatal outcomes, American Journal of Perinatology, vol. 15, No. 3, Mar. 1998, pp. 177-181.

Denney, Jeffrey M. et al., Prevention of preterm birth, Women's Health, (2008) 4(6), 625-638.

* cited by examiner

ADMINISTRATION OF N,N-DIMETHYLACETAMIDE FOR THE TREATMENT OF PRETERM BIRTH

CROSS-REFERENCE TO RELATED APPLICATION

This application claims benefit of provisional application No. U.S. 61/571,433 filed on Jun. 28, 2011.

SUMMARY OF THE INVENTION

The subject invention is directed to the treatment of inflammation and inflammatory disorders by the administration of a compound of general formula, but not limited to N,N-dimethylacetamide (DMA) and its monomethylated metabolites. The compounds can be in various formulations (including but not limited to: liquid, transdermal patches, ointments, paste, creams, gels, powders, sprays, intradermal, i.v., aerosol and nebulized forms, pills with solutions; ophthalmic formulation, ear drops, eye ointments, powders and solutions) and are useful in preventing or treating inflammatory conditions produced by diseases, drugs (natural compounds and synthetics), surgery and trauma. These diseases or conditions will include but will not be limited to:
1) Pre-term birth/premature delivery
2) Cardiovascular—atherosclerotic diseases (angina pectoris and myocardial infarction), thrombosis, ischemia/reperfusion syndrome, myocarditis, angiitis; vasculitis
3) Dermatologic diseases—associated with inflammation such as psoriatic arthritis, dermatitis, psoriasis, eczema, acne, dermatitis herpetiformis, dermatomyositis, pemphigus vulgaris, bullous pemphigoid, Stevens-Johnson syndrome, toxic epidermal necrolysis, rosacea, scleroderma. Alopecia areata, urticaria
4) Musculoskeletal—rheumatoid arthritis (juvenile and adult), synovitis, osteoarthritis, degenerative joint disease, one or more connective tissue diseases, polymyalgia rheumatica, ankylosing spondylitis, polymyositis, bursitis, fibromyalgia, gout, neuralgia, chronic fatigue syndrome
5) Infection—Any type of infection, including, but not limited to sepsis, influenza A-induced tissue inflammation, systemic inflammatory reactive syndrome, herpes simplex 1 and 2, HIV, AIDS, hepatitis, impetigo
6) Autoimmune—systemic lupus erythematosus, Sjogren's syndrome, Goodpasture's syndrome, Myasthenia gravis, SLE, Bechet's diseases,
7) Gastrointestinal—gingivitis, periodontal diseases, gastritis, inflammatory bowel diseases such as diverticulitis, celiac disease, proctitis, gastroenteritis, pancreatitis, mastocytosis, Crohn's disease, ulcerative colitis, microscopic colitis, indeterminant colitis, irritable bowel disorder, irritable bowel syndrome and distal proctitis.
8) Respiratory tract including allergic rhinitis, nasal polyps, sinusitis, asthma, adult respiratory distress syndrome, chronic obstructive pulmonary disease, pulmonary fibrosis and pneumonia bronchitis, sarcoidosis
9) Neurodegenerative diseases or neurological disorders or inflammation in the CNS. These include but will not be limited to stroke, traumatic brain injury, spinal cord injury, Alzheimer's disease, fronto-temporal dementias, peripheral neuropathy, Parkinson's disease, dementia with Lewy bodies, Huntington's disease, amyotrophic lateral sclerosis, schizophrenia, Gullian-Barre syndrome, encephalitis, idiopathic inflammatory demyelinating diseases and multiple sclerosis.
10) Genitourinary—endometriosis, eosinophilic cystitis, glomerulonephritis, polycystic ovary disease
11) Cancer—including malignant neoplasia (solid and non-solid), metastasis
12) Endocrine—Diabetes (and one of its major consequences, obesity), thyroiditis
13) Other—Transplant rejection, graft-vs-host disease (acute and chronic), post-traumatic
14) Poison ivy and poison oak inflammation

DETAILED DESCRIPTION OF THE INVENTION

Figure 1A:
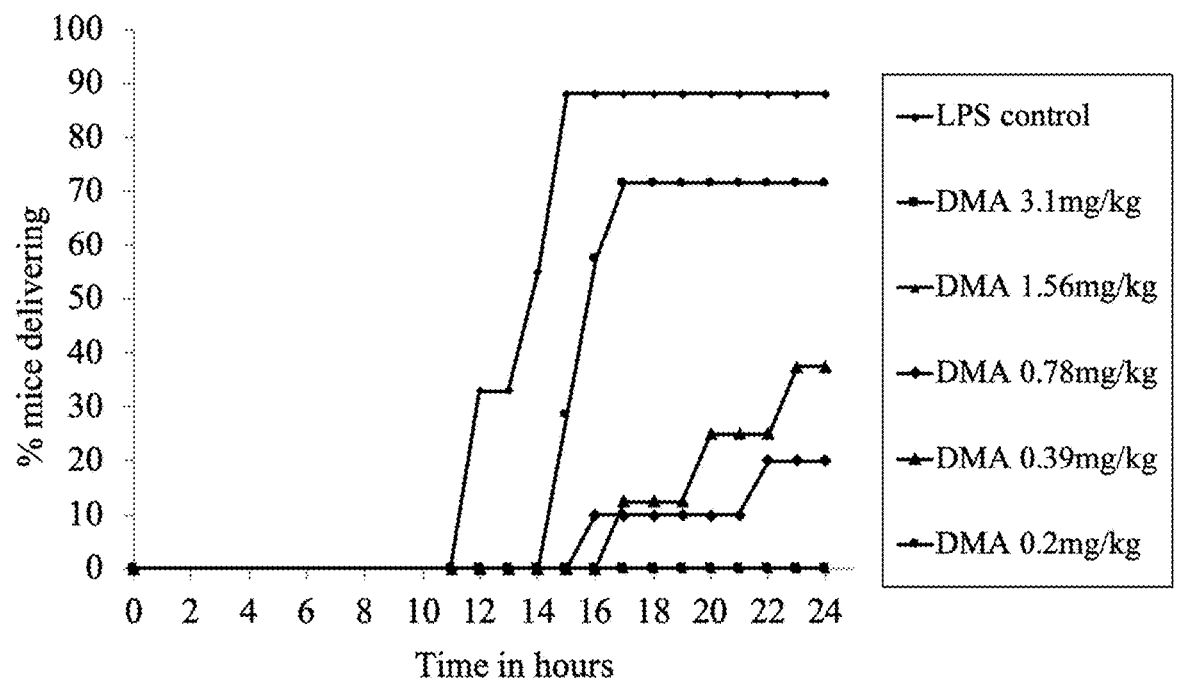
FIG. 1. DMA prevents preterm birth. A dose response relationship exists between DMA and the number of LPS-induced mice rescued from preterm delivery and between DMA and the number of pups rescued from LPS-triggered spontaneous abortion.

The subject invention is directed to the administration of DMA and its monomethylated metabolites for the treatment of inflammation and inflammatory disorders. The compounds can be in various formulations (including but not limited to: liquid, transdermal patches, ointments, paste, creams, gels, powders, sprays, intradermal, i.v., aerosol and nebulized forms, pills with solutions; ophthalmic formulation, ear drops, eye ointments, powders and solutions) and are useful in preventing or treating inflammatory conditions produced by diseases, drugs (natural compounds and synthetics), surgery and trauma. These diseases or conditions will include but will not be limited to those listed in Summary of the Invention. The treatment is intended for a variety of mammals, such as premature neonates to adult humans.

The effective daily dose of DMA and its monomethylated metabolites ranges from approximately 1 µg/kg to 5 mg/kg body weight. Further, the time over which DMA or one of its monomethylated metabolites is administered may vary as is well known in the art to achieve the desired results. For example, DMA may be administered as an aerosol from about 10 minutes to about 1 hour per treatment regimen, 3 times daily, or until the desired daily dosage is fully administered.

DMA may be mixed with a pharmaceutically acceptable dilutant. Such examples include saline solution, DMSO, an alcohol, or water. Such carriers are well known in the art, and the specific dilutant employed may be varied depending upon factors such as size of the subject being treated, treatment dose, and the like. The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention.

Methods

Experimental Design

In vivo Studies of Effect of DMA on PTB

A total of 48 timed-pregnant mice weighing between 27 and 36 grams were given intraperitoneal (i.p.) injections of 50 mg/kg LPS (serotype 026: B6; Sigma) dissolved in 500 µL of phosphate-buffered saline (PBS) on embryonic day (E) 15.5 (t=0 hours). Mice were then randomly assigned to the control group or one of five treatment groups. At t=−0.5 hours and t=10 hours they were injected with either 0.5 ml of PBS (control group) or 0.1 ml of increasing concentrations (6.25%, 12.5%, 25%, 50% and 100%) of N,N-dimethylacetamide (DMA) (treatment groups). Additionally, a sixth group of four animals received i.p. injections of 0.5 ml PBS in lieu of LPS at the same time points and served as sham (Table 1).

TABLE 1

Groups of mice in the DMA dose response studies.

| | Group | | | | | | |
|---|---|---|---|---|---|---|---|
| | Control | DMA Treatment | | | | | Sham |
| | | 6.25% | 12.5% | 25% | 50% | 100% | |
| Received 50 mg/kg LPS | Yes | Yes | Yes | Yes | Yes | Yes | No |
| Number of Mice | 9 | 7 | 8 | 10 | 6 | 8 | 4 |

After the injection at t=10 hours, mice were continually monitored; time of delivery of the first pup and number of pups dropped over time were recorded. Experiments were allowed to continue to t=24 hours. All mice were sacrificed by carbon dioxide asphyxiation. The mice were autopsied at the end of experiments to confirm pregnancy and to determine the number of pups retained in utero. Placenta and uteri were harvested and stored.

Histologic Analysis of Effect of DMA on Inflammatory Cell Infiltration

Placentas were harvested immediately after necropsy and fixed in formalin. Fixed tissues were dehydrated and paraffin embedded, sectioned at 4 µm and stained with hematoxylin and eosin. All slides were examined by three blinded observers and graded for extent of inflammatory cell infiltration: slides with an average number of 0-5 neutrophils per high power field observed with the 40× objective in the three most active fields found were graded 1; slides with greater than an average of 6 to 50 neutrophils in the three most active high power fields were graded 2; and slides with greater than 50 neutrophils on average in the three most active high power fields were graded 3.

Gel Electrophoresis

Frozen placentas and uteri from each group were allowed to thaw on ice. Each tissue was then transferred to a Kontes glass homogenizer (Fisher Scientific) and 0.3 ml ice cold lysis buffer was added. Samples were homogenized manually on ice for two minutes at intervals of 15 minutes. This process was continued for a period of two hours. The probe was thoroughly cleaned after each sample. The homogenate was transferred to 1 ml eppendorf tubes and centrifuged at 10,000 rpm for five minutes. The protein content of the supernatant was determined using Bradford assay with bovine serum albumin as the protein standard.

A volume corresponding to 30 µg protein of the supernatant was added to a tube containing 3 µl NuPAGE® LDS sample buffer (4×) and 1 µl NuPAGE® sample reducing agent (10×). The final volume was made up to 12 µl with distilled water, and then the samples were reduced at 95° C. for 5 minutes. Gel electrophoresis was carried out in an XCell SureLock mini cell apparatus using 12 well NuPAGE® Bis-Tris Gel for protein separation. The gel was allowed to run for 45 minutes with 3-(N-morpholino)propanesulfonic acid (MOPS) running buffer. Proteins were then transferred to a polyvinylidene difluoride (PVDF) membrane.

Immunoblotting

The PVDF membranes were wetted with Tris-buffered saline with 0.1% Tween-20 (TBS-T), pH 7.8 for ten minutes, and were then blocked with 5% skim milk powder in TBS-T solution for two hours. Next, the membranes were incubated with primary antibodies diluted in the blocker solution overnight at 4° C. They were then washed with TBS-T thrice at intervals of 15 minutes at room temperature (RT). The membranes were incubated with a 1:1000 dilution of secondary antibody, anti-rabbit IgG, horseradish peroxidase-linked whole antibody, in blocker solution at RT for two hours. The membranes were washed again with TBS-T three times for 15 minutes and treated with the ECL Plus Western blotting detection system. Chemifluorescence was detected by exposure to an autoradiography film. Upon development of the x-ray film, the membranes were subjected to repeated washings with TBS-T and stored in TBS-T at 4° C. The membranes were incubated with stripping buffer for 20 minutes at RT, thoroughly washed and incubated with anti-GAPDH primary antibody (1:1000) and the same procedure was repeated for the gel loading control. The protein content was quantified using Image J software (NIH). The density values of housekeeping protein GAPDH immunoblots were used for normalization.

Immunocytochemical Analysis of the Effect of DMA on NF-κB Translocation

Immunocytochemical analysis was employed to assess the intracellular localization of NF-κB in the absence or presence of graded concentrations of DMA. RAW 264.7 cells were seeded in 12-well plates and were allowed to adhere overnight at 37° C. Cells were grown with or without LPS (100 ng/ml) in the presence or absence of 0.01 or 1 µM DMA for two hours. After treatments, cells were fixed with 2% phosphate-buffered formaldehyde (pH 7.4) for 15 min and washed three times with PBS. Cells were then permeabilized with 0.2% Triton X-100 and nonspecific binding sites were blocked with 10% normal goat serum (NGS) for 20 min. This step was followed by washing the cells with 1% BSA in PBS and incubating with anti-NF-κB p65 primary antibodies overnight at 4° C. Incubation with secondary antibody using goat anti-rabbit immunoglobulin G (IgG) conjugated with Alex fluor 594 was performed for one hour. Normal blocking serum without primary antibody was used as negative control. To visualize the nuclei, cells were counterstained with DAPI. NF-κB translocation was observed under an immunofluorescence microscope (Nikon, Melville, N.Y.).

Results

Dose Dependent Effect of DMA on Rate of LPS-Triggered PTB

Timed pregnant E15.5 C57BL/6 control mice treated with LPS and PBS injections (n=9) developed preterm labor and delivery at a rate of 89% (eight out of nine mice). Among the eight mice responding to the LPS, the mean time of delivery was 14.3 hours. The effect of DMA on rates of preterm birth was tested by treating additional E15.5 C57BL/6 mice with a series of various doses of DMA. At the two highest doses, 3.1 and 1.56 mg/kg, 0 out of 8 and 0 out of 6 mice delivered, respectively. Thus 100% prevention of PTB was achieved at the highest doses of DMA. At the next dose of 0.78 mg/kg, 2 out of 10 (20%) mice delivered with the average time of delivery being 19.4 hours. At 0.39 mg/kg, 3 out of 8 (37.5%) mice delivered with 20.1 hours as the average time of delivery. At the lowest dose (0.2 mg/kg), 5 out of 7 (71.43%) mice delivered and the average time of delivery was 16.1 hours (Table 2; FIG. 1A).

Figure 1B:
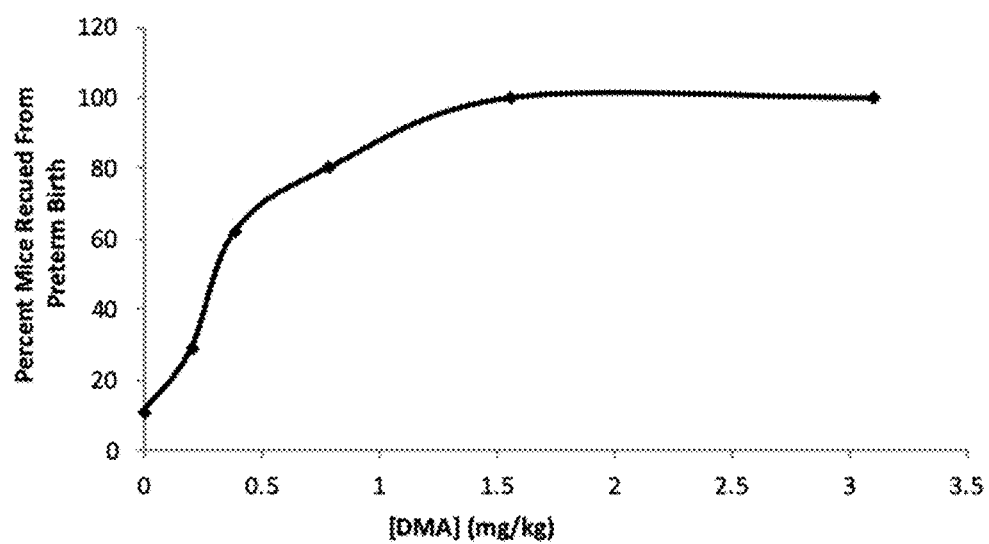

Statistically significant differences in the percent mice delivering in the control group and in the groups treated with all the doses of DMA except the lowest one were found (p<0.05), using Dunnett's multiple comparison test with the number of mice reaching preterm delivery decreasing as the dose of DMA was increased. Furthermore, one way ANOVA revealed statistically significant differences in the average delivery times among those mice developing PTB in the control group and the groups treated with all the DMA doses but the lowest in a dose dependent fashion (p<0.05). Using the Fisher exact test to compare the number of animals delivering prematurely in the DMA treated groups (3.1, 1.56, 0.78, 0.39 and 0.2 mg/kg) to the LPS control group, statistical significance was reached for all groups except the one receiving the lowest dose (p<0.001, p<0.01, p<0.01, p<0.05; p NS, respectively). At 0.2 mg/kg there was no significant difference in the number of mice delivering vs. control (p=0.5); hence, we did not decrease the DMA dose further. The statistical significance of the effect of all but the lowest dose of DMA on the rate of premature deliveries over time was confirmed by the log-rank (Mantel-Cox) or Gehan-Breslow-Wilcoxon test. P values for the five doses of DMA used, from highest to lowest were p<0.001, p<0.001, p<0.05, p<0.05, p NS, respectively. Finally, a classical dose-response relationship between DMA and the number of mice rescued from preterm birth is observed (FIG. 1B).

Dose Dependent Effect of DMA on Rate of LPS-Triggered Spontaneous Abortion

Figure 1C:
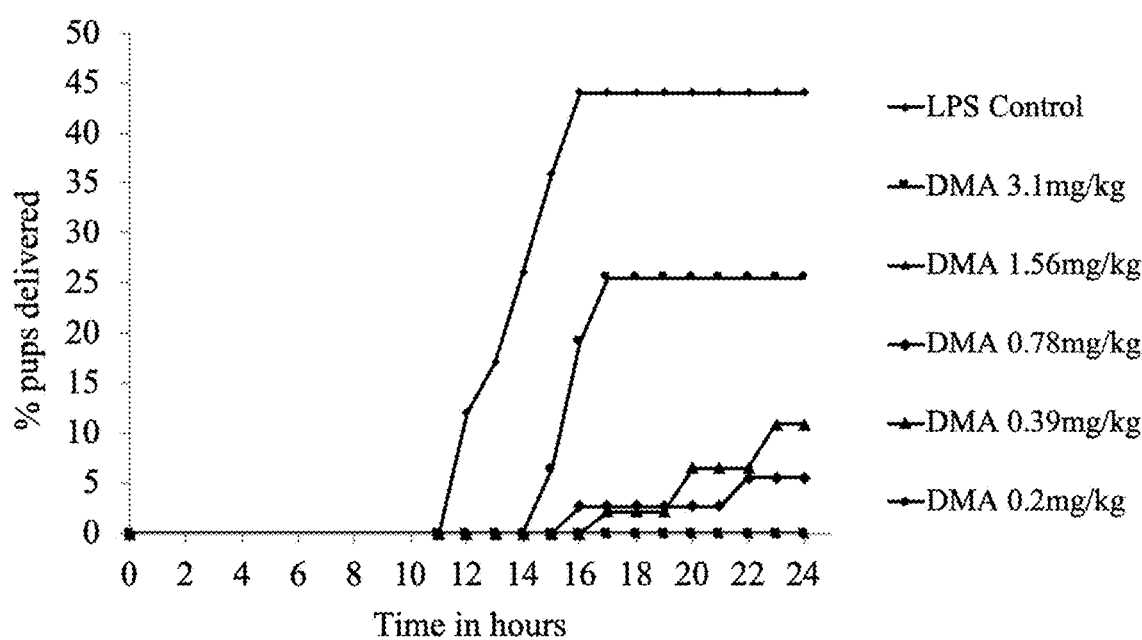
Figure 1D:
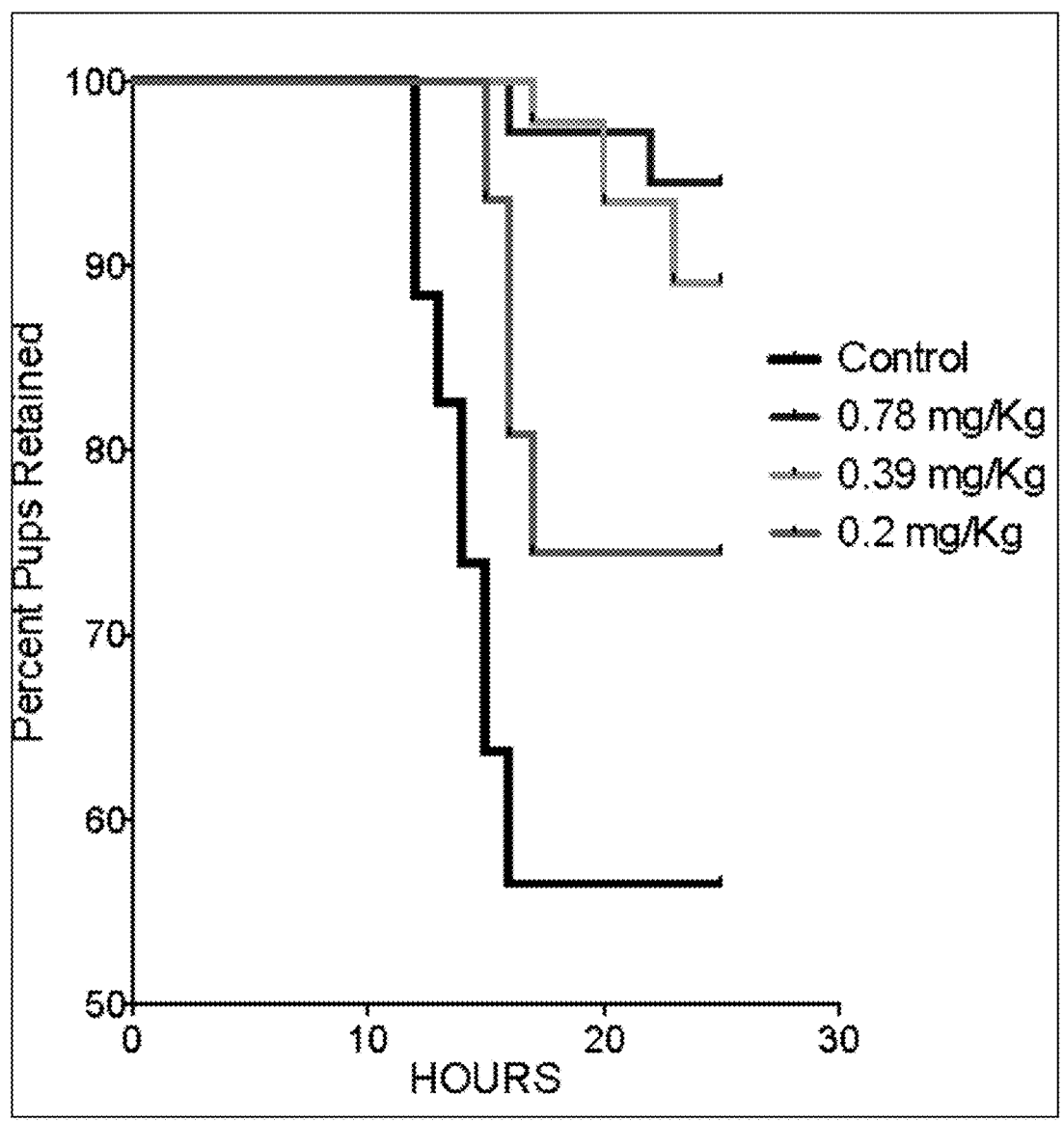

In addition to its dramatic influence on rates of LPS induced PTB, DMA had an even more impressive effect on rates of pups lost to spontaneous preterm delivery. Among the LPS treated controls (n=69 pups), 30 pups (43.5%) were lost secondary to preterm delivery. No pups were lost after treatment with 3.1 mg/kg DMA (n=52) or with 1.56 mg/kg DMA (n=47). After treatment with 0.78 mg/kg, 4 out of 73 (5.5%) pups were spontaneously aborted. At 0.39 mg/kg of DMA, 5 out of 46 (10.9%) were lost and 12 out of 47 (25.5%) pups were dropped at 0.2 mg/kg (Table 2, FIG. 1C). These results are also represented with Kaplan Meier survival curves (FIG. 1D).

Figure 1E:
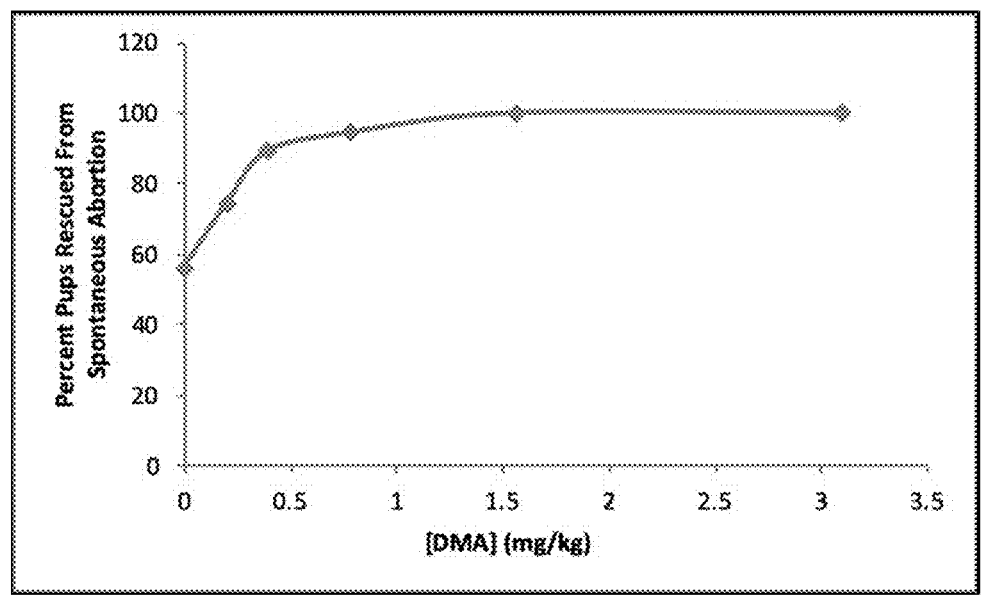

By Chi-Square analysis, the number of pups spontaneously aborted in the DMA treated groups was significantly lower than in the control group (p<0.001) for all doses except the lowest dose, 0.0.2 mg/kg DMA. Moreover, Dunnett's multiple comparison test indicated that there was a statistically significant difference in the percent pups lost at the different doses vs. control (p<0.05) (FIG. 1C). The effect of all doses of DMA on the rate of pups being prematurely delivered was significant by log-rank test (p<0.0001, p<0.0001, p<0.0001, p<0.0001 and p<0.01, corresponding to highest to lowest doses). Finally, a classic dose-response relationship between DMA and the number of pups rescued from spontaneous abortion is observed (FIG. 1E).

Figure 2:
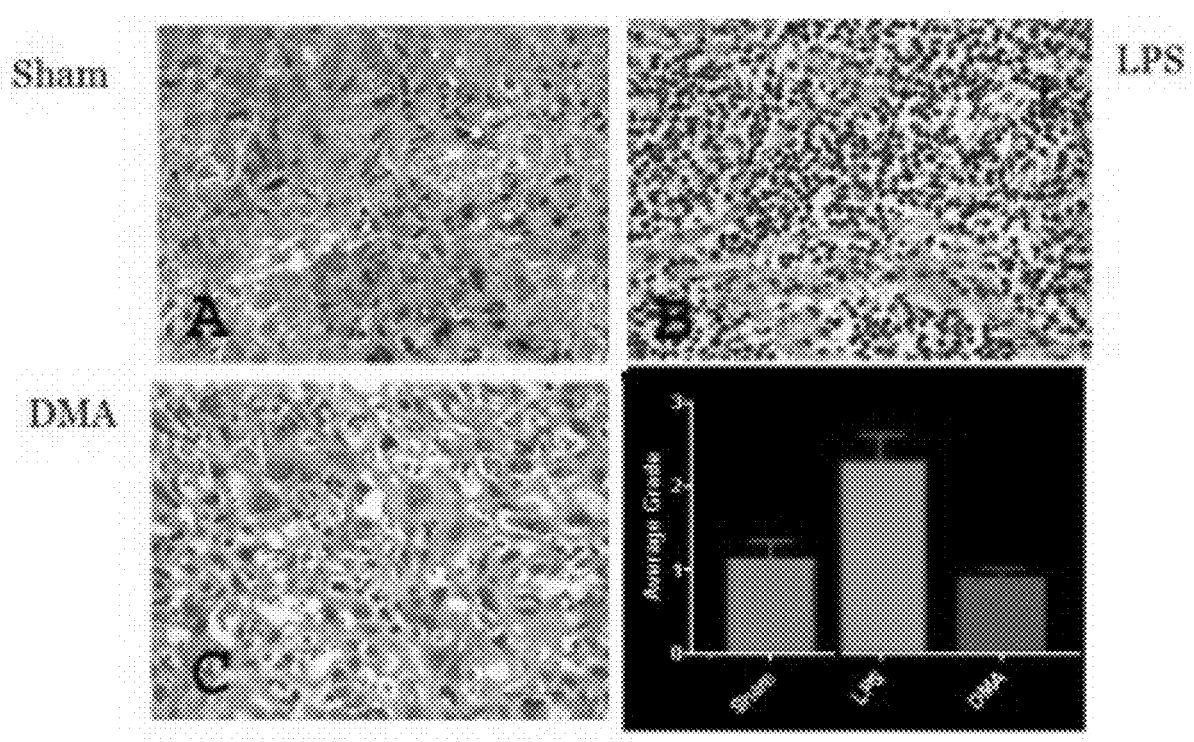
FIG. 2. DMA suppresses LPS-triggered inflammation in mouse placenta. Histologic analysis showed attenuation of LPS-linked inflammation in placentas from mice rescued from PTB by DMA.

Effect of DMA on Recruitment of Inflammatory Cells to Gestational Tissue Vasculature Harvested placentas from mice subjected to sham injections (n=4), LPS plus PBS (n=4) and LPS plus DMA (n=4) showed vastly different degrees of intravascular inflammatory cell recruitment histopathologically. In FIG. 2, Panel C shows a representative microscopic section of placental labyrinth collected from a mouse treated with LPS, but then rescued from preterm labor and delivery with 1.56 mg/kg DMA. Inflammatory cells are scant. In fact the histopathological picture is indistinguishable from the representative micrograph produced with a placenta removed from a negative control mouse treated with only PBS (FIG. 2, Panel A). A representative section from a mouse that developed preterm labor and delivery subsequent to treatment with LPS, in contrast, shows a dense collection of marginating polymorphonuclear neutrophils (FIG. 2, Panel B). The results of a graded quantitative analysis performed by three blinded observers, including a placental pathologist, are shown. The increase in the number of inflammatory cells in placentas from LPS plus PBS treated mice as compared to sham negative control animals is statistically significant (p<0.01). Similarly, the reduction in the number of leukocytes in placentas from mice treated with LPS, but ultimately rescued from PTB with DMA, as compared to mice induced to labor with LPS, is highly significant (p<0.01).

Effect of DMA on Cytokine Expression.

Figure 3:
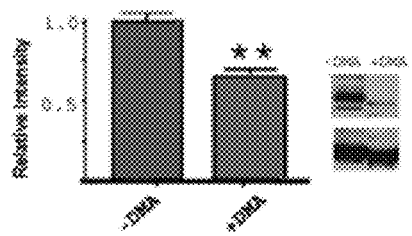
FIG. 3. The effect of DMA on expression of LPS-induced pro-inflammatory cytokines in a murine model of infection-associated preterm birth. DMA suppressed LPS-induced IL-1$\beta$, IL-6 and TNF$\alpha$ in vivo.
Figure 3:
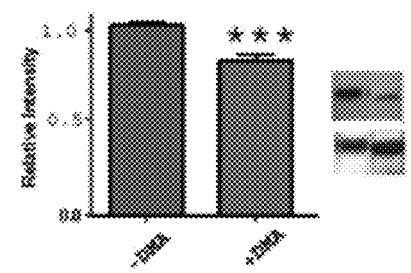
Figure 3:
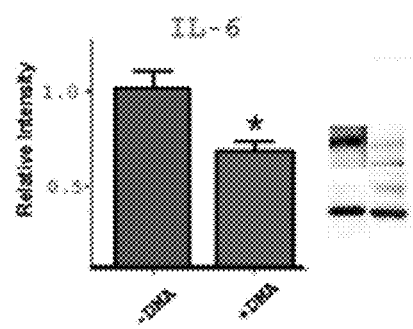
Figure 4:
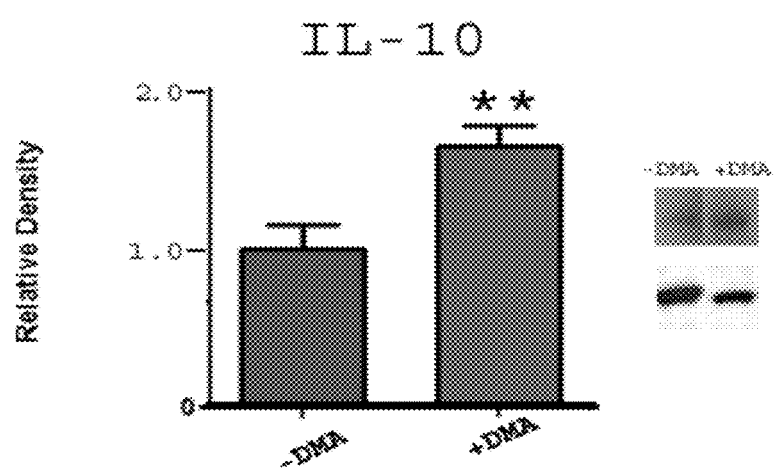
FIG. 4. The effect of DMA on the expression of IL-10 in a murine model of infection-associated preterm birth. DMA enhanced expression of LPS-induced IL-10 in vivo.

Several pro-inflammatory mediators were selected and tested for changes in expression at the protein level resulting from DMA rescue from LPS induced PTB. As compared to levels of expression in placental tissue from mice that developed LPS-triggered PTB, IL-1β expression in placentas from DMA rescued mice was significantly reduced (p<0.01) (FIG. 3A). Similar results were found for TNF-α (p<0.001) and IL-6 (p<0.05) (FIG. 3). Interestingly, expression of the regulatory cytokine IL-10 increased significantly in placental tissue harvested from mice rescued from PTB with DMA (p<0.001) (FIG. 4). Tissue from mice treated with LPS alone is indicated as −DMA, while tissue from mice rescued from PTB with DMA is indicated as +DMA in these figures. Top bands are immunoblots of cytokine proteins; bottom bands are immunoblots of gluteraldehyde phosphate dehydrogenase (GAPDH) gel loading controls.

Effect of DMA on Nuclear Translocation of NF-kB in LPS-Stimulated Macrophages

Figure 5:
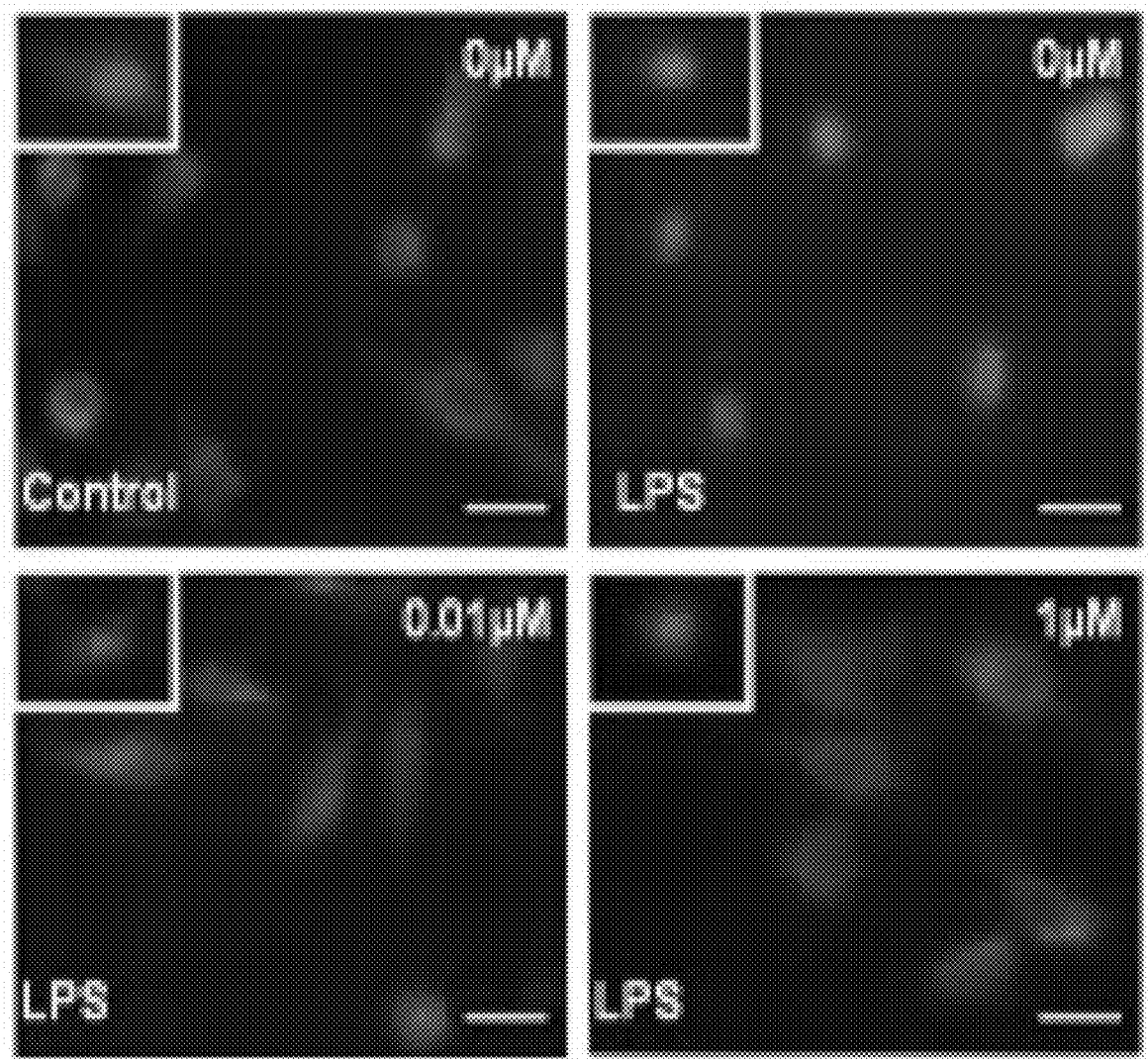
FIG. 5. DMA prevents nuclear translocation of NF-$\kappa$B in vitro. DMA prevented nuclear translocation of NF-$\kappa$b in a cultured macrophage cell line stimulated with LPS.

LPS stimulation in RAW 264.7 cells induces activation of the NF-κB signaling pathway, which is critical in cytokine release (Ulloa et al., 2002). To determine whether DMA plays a role in the NF-κB signaling pathway, NF-κB translocation was assessed by immunostaining the p65 unit of NF-κB. FIG. 5A demonstrates that NF-κB was primarily localized in the cytoplasm, indicated by a prominent red stain and a distinct hollow in the nucleus. However, treatment with LPS leads to translocation of NF-κB into the nucleus, as indicated by profound nuclear staining in FIG. 5B. DMA at concentrations 0.01 µM and 1 µM clearly reduced nuclear staining in comparison to cells treated with LPS alone, with greater inhibition of NF-κB translocation into the nucleus noted with the higher concentration of DMA (FIGS. 5C and 5D). To confirm that DMA did not affect cell viability at the concentrations utilized for the study, cells were also grown in the absence or presence of LPS at varying concentrations of DMA and survival was tested. No significant effect on cell viability was detected at any of these concentrations.

Discussion

The data presented show a clear role for DMA as an anti-inflammatory agent. In the infection-associated preterm birth bioassay, a dose-response relationship was observed both for the effect of DMA on the percent of mice delivering and the effect of the compound on the percent of pups dropped. The mechanism of action of DMA is clearly suppression of an inflammatory pathway. In the histological analysis of placental tissues, DMA abolished the robust inflammatory cell infiltrate triggered by LPS. Immunoblot analysis revealed that expression levels of the pro-inflammatory cytokines IL-1β, TNFα, and IL-6 in gestational tissues from LPS-induced mice are significantly decreased by DMA. Moreover, DMA increased expression of the anti-inflammatory mediator, IL-10, in these tissues. Finally, DMA prevented nuclear translocation of NfF-kB.

DMA is currently used as an organic solvent, a cryopreservative for platelets (Odink et al. 1977) and a solvent for a novel anti-retroviral agent (Aungst et al. 2000). DMA, administered i.p. for three days at doses of 150 mg/kg or 300 mg/kg, does not affect P450-dependent monooxygenase or phase II enzyme activities. MMA also did not induce any hepatic monooxygenases in rat. A study by Beyhl and Linder (1981) also showed that in liver homogenate DMA had no effect on liver mixed-function oxidase and cytochrome c reductase activities. Importantly, it is given in intravenous busulfan to pediatric oncologic patients at doses many-fold higher than those shown to suppress inflammation in this work with no adverse effect (Hempel 2007).

DMA may function as a pro-drug. It is metabolized through sequential demethylation by liver enzymes before it is eliminated. The major urinary metabolites in rats are 60-70% N-monomethylacetamide (MMA), 7-10% N-hydroxymethylacetamide, 7-10%, acetamide and some residual DMA. However, the only metabolite in humans is MMA. The plasma half life of DMA is very short and DMA is undetectable in plasma after 12 hours, whereas that of its main metabolite, MMA, is much longer. In rats it is about 2.2 hours and a significant amount of MMA was still present in plasma after 24 hours (Hundley 1994).

A method of attenuating the excessive inflammatory response triggered by the toll-like receptors represents a very valuable, novel therapeutic approach to a variety of inflammatory disorders (Weighardt and Holzmann 2007), including sepsis (Puneet et al. 2010). DMA has a clear therapeutic advantage over known anti-inflammatory agents, such as TNFα monoclonal antibodies and nitric oxide synthase inhibitors, which compromise the host's ability to fight off infections (Wadgaonkar et al. 2009).

Many inflammatory disorders are likely to be amenable to treatment with DMA without compromise of the host's immune system. In fact bacterial clearance is improved when over-exuberant inflammation is held in check as is evidenced by the favorable effect obtained when TLR-linked sphingosine kinase is inhibited (Puneet et al. 2010). As inflammation is implicated in an extremely broad spectrum of disorders, ranging from cancer to neurodegenerative diseases, the potential clinical impact of this molecule as an anti-inflammatory agent is striking.

TABLE 2

Effect of varying doses of DMA on preterm birth.

| Group | Control | DMA Treatment (mg/kg) | | | | | Sham |
| --- | --- | --- | --- | --- | --- | --- | --- |
| | | 0.2 | 0.39 | 0.78 | 1.56 | 3.1 | |
| Received 50 mg/kg LPS | Yes | Yes | Yes | Yes | Yes | Yes | No |
| Number of Mice | 9 | 7 | 8 | 10 | 6 | 8 | 4 |
| Number of mice that delivered | 8 | 5 | 3* | 2** | 0** | 0*** | 0 |
| Number of pups dropped | 30 | 12 | 5*** | 4*** | 0*** | 0*** | 0 |
| Number of pups retained | 39 | 35 | 41 | 69 | 47 | 52 | 0 |

REFERENCES

Aungst B J, Nguyen N H, et al. Pharm Res 17:1175-1180, 2000.
Beyhl F E and Lindner E. Food Cosmet Tox 19:627-629, 1981.
Hempel G, Oechtering D, et al. J Clin Onc 25:1772-1778, 2007.
Hundley S G, Leider P H et al. Tox Lett 73:213-215, 1994.
Odink J and Sprokholt R. Cryobiology 14:519-528, 1977.
Puneet P, Yap C T et al. Science 328:1290-1294, 2010.
Ulloa M, Ochani M, et al. PNAS 99:12351-12356, 2002.
Wadgaonkar R, Patel V, et al. Am J Physiol Lung Cell Molec Phys 296:L603-L613, 2009.
Weighardt H and Holzmann B. Immunobiol 212:715-722, 2007.

What is claimed is:

1. A method of preventing preterm birth comprising administering a composition comprising N,N-dimethylacetamide ("DMA") to a pregnant human, wherein the DMA is administered at a dose ranging from approximately 1 μg/kg to 5 mg/kg body weight of the pregnant human.

2. The method of claim 1, wherein the composition further comprises a pharmaceutically acceptable diluent.

3. The method of claim 2, wherein the pharmaceutically acceptable diluent comprises water.

4. The method of claim 2, wherein the pharmaceutically acceptable diluent comprises saline solution, dimethyl sulfoxide ("DMSO"), an alcohol or water.

5. The method of claim 1, wherein the composition is administered intravenously.

6. The method of claim 1, wherein the composition comprises an aqueous solution and is administered intravenously.

7. The method of claim 1, wherein the composition is administered intraperitoneally.

8. The method of claim 1, wherein the composition is formulated as an intravenous solution.

9. The method of claim 1, wherein the composition is formulated as a transdermal patch, an ointment, a paste, a cream, a gel, a powder, a spray, an aerosol, a pill, or a solution.

10. The method of claim 1, wherein DMA is the sole active agent for the prevention of preterm birth in the composition.

11. The method of claim 2, wherein DMA is the sole active agent for the prevention of preterm birth in the composition.

12. The method of claim 3, wherein DMA is the sole active agent for the prevention of preterm birth in the composition.

13. The method of claim 4, wherein DMA is the sole active agent for the prevention of preterm birth in the composition.

14. The method of claim 5, wherein DMA is the sole active agent for the prevention of preterm birth in the composition.

15. The method of claim 6, wherein DMA is the sole active agent for the prevention of preterm birth in the composition.

16. The method of claim 7, wherein DMA is the sole active agent for the prevention of preterm birth in the composition.

17. The method of claim 8, wherein DMA is the sole active agent for the prevention of preterm birth in the composition.

18. The method of claim 9, wherein DMA is the sole active agent for the prevention of preterm birth in the composition.

* * * * *